United States Patent
Gazda et al.

(10) Patent No.: US 7,413,871 B2
(45) Date of Patent: Aug. 19, 2008

(54) SCORING METHOD FOR DETERMINING PANCREAS SUITABILITY FOR ISLET ISOLATION

(75) Inventors: Lawrence Gazda, Xenia, OH (US); Barry Smith, New York, NY (US); Albert Rubin, New York, NY (US)

(73) Assignee: The Rogosin Institute, New York, NY (US)

( * ) Notice: Subject to any disclaimer, the term of this patent is extended or adjusted under 35 U.S.C. 154(b) by 250 days.

(21) Appl. No.: 11/273,737

(22) Filed: Nov. 14, 2005

(65) Prior Publication Data

US 2006/0121445 A1    Jun. 8, 2006

Related U.S. Application Data

(60) Provisional application No. 60/629,227, filed on Nov. 17, 2004.

(51) Int. Cl.
*C12Q 1/02* (2006.01)
(52) U.S. Cl. ....................................................... 435/29
(58) Field of Classification Search ...................... None
See application file for complete search history.

(56) References Cited

OTHER PUBLICATIONS

Krickhahn et al, "The Morphology of Islets Within the Porcine Donor Pancreas Determines the Isolation Result: Successful Isolation of Pancreatic Islets Can Now Be Achieved From Young Market Pigs," (Cell Transplantation), vol. 11, 2002, pp. 827-838.*

* cited by examiner

*Primary Examiner*—Robert B. Mondesi
*Assistant Examiner*—Amanda P Wood
(74) *Attorney, Agent, or Firm*—Fulbright & Jaworski LLP

(57) ABSTRACT

The invention relates to a method for evaluating a pancreas as a source of therapeutically useful islets. A scoring system is set forth whereby 5 criteria are listed. If three criteria are positive, then the pancreas is a suitable source of therapeutically useful islets.

13 Claims, 1 Drawing Sheet

SCORING METHOD FOR DETERMINING PANCREAS SUITABILITY FOR ISLET ISOLATION

RELATED APPLICATION

This application claims priority of application Ser. No. 60/629,227, filed Nov. 17, 2004, incorporated by reference in its entirety.

FIELD OF THE INVENTION

This invention relates to methods for improving the quality and quantity of yield of islets. Islets are found in pancreases of animals, and the invention relates to methods for determining if a pancreas will give a good yield of islets.

BACKGROUND AND PRIOR ART

It is now established that islet replacement therapy is a viable approach for treatment of patients with various disorders. These include cancer patients undergoing upper abdominal exenteration (Tzakis, et al., *Lancet*, 336: 402-405 (1990)); pancreatitis (Clayton, et al., *Transplantation*, 76: 92-98 (2003); Farney, et al., *Surgery*, 110: 427-437 (1991); Fontes, et al., *Transplant Proc*, 24: 2809 (1992); Obenholzer, et al., *Transplantation*, 69: 1115-1123 (2000); Robertson, et al., *Diabetes*, 50: 47-50 (2001)), and insulin-dependent patients, where islet transplantation is a therapeutic option (Goss, et al., *Transplantation*, 74: 1761-1766 (2002); Ricordi, et al., *Transplantation*, 75: 1524-1527 (2003); Ryan, et al., *Diabetes*, 50: 710-719 (2001); Shapiro, et al., *N. Engl. J. Med*, 343: 230-238 (2000)).

Due to the usefulness of islets in therapy, as is indicated, supra, there is, of course interest in developing ways to isolate them. While there are many reports on isolation of islets using the automated method (Brandhorst, et al., *Exp. Clin. Endocrinol Diabetes*, 103 Suppl. 2: 3-14 (1995); Cui, et al., *Cell Transplant*, 6: 48-54 (2001); Marchetti, et al., *Transplantation*, 52: 209-213 (1991); Miyamoto, et al., *Cell Transplant*, 7: 397-402 (1998); Nielsen, et al., *Comp. Med.*, 52: 127-135 (2002); Swanson, et al., *Hum. Immunnol*, 62: 73 9-749 (2001); Toomey, et al., *Brit. J. Surg.*, 80: 240-243 (1993); Toso, et al., *Cell Transplant*, 9: 297-305 (2000); Wennberg, et al., *Transpalnt. Proc.*, 33: 2537 (2001)), isolation of islets remains notoriously difficult. For example, Bosta, et al., *J. Investig Med*, 43: 555-566 (1995); Krickhahn, et al., *Cell Transplant*, 11: 827-838 (2002); Krickhahn, et al., *Ann Transplant*, 6: 48-54 (2001), O'Neil, et al., *Cell Transplant*, 10: 235-246 (2001), and White, et al., *Horm. Metab. Res*, 31: 579-524 (1999), all discuss problems with respect to this.

The invention which is set forth in the disclosure which follows is directed to a method for maximizing the probability of successful islet yield. It has been determined that via the use of the scoring system set forth herein, one can maximize the opportunity of securing a good yield of islets from any given pancreatic islet isolation.

How this is accomplished will be seen in the disclosure which follows.

BRIEF DESCRIPTION OF THE FIGURES

FIG. 1A shows a micrograph of a pancreas which, using the method of the invention, has a score of +3 and thus qualifies as a useful pancreas, which FIG. 1B shows a micrograph of one with a score of −1, which does not qualify.

DETAILED DESCRIPTION OF PREFERRED EMBODIMENTS

EXAMPLE 1

Figure 1:
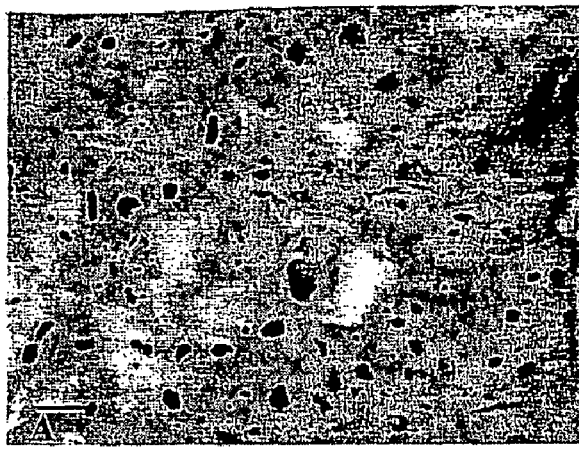
Figure 1:

The animals used in the examples which follow were sows, over two years old, with multiple parities. The animals were stunned electrically and exsanguinated. Viscera were then removed for pancreatic dissection. The length of time between the electric stun, to placement of the pancreas in cold Hank's Balanced Salt Solution("HBSS") was generally 10-15 minutes. Cold ischemia times ranged from 15-20 minutes.

To elaborate on this procedure, the entire pancreas was retrieved, and then the annular ring around the portal vein was cut, transversally at the connection between the right and left lobes, in order to provide a section of biopsy tissue about 2-5 mm thick.

The biopsied tissue sections were cut in half and placed, in either HBSS or in dithizone solution ("DTZ"), in accordance with Ricordi, et al., in Ricordi, et al., ed. *Pancreatic Islet Cell Transplantation* (Austin: R.G. Landes Company, 1992), 132-142.

The pancreas was then placed in HBSS to which 2% heat inactivated porcine serum ("PS") had been added, and then transported to a laboratory for islet isolation.

Pancreas biopsies were then evaluated, to determine if they were suitable for islet isolation. Five variables were assessed. In each case, a score of either +1 or −1 was assigned to the variable, as is explained infra.

First, warm ischemia time was determined. This is defined as the time between initiation of exsanguination and placement of the pancreas in a cold preservative solution. If this is accomplished in 15 minutes, or less a score of +1 was assigned. If more than 15 minutes transpire, a score of −1 was assessed. While a warm ischemia time of up to 20 minutes will sometimes produce a good yield of islets, the chances of succeeding drop after a warm ischemia time of 15 minutes.

For the second criteria, the color of the pancreas was observed. Color variation between pancreases may be the result of several factors. For example, if a pancreas displays venous congestion, as a result, e.g., of the electrocution of animals, or of a stress response, then that pancreas does not display qualities that make it desirable as an islet donor. Both conditions can lead to blood pooling within the pancreas, release of hemoglobin, and its diffusion into extracellular space. In turn, this leads to a change in color of the organ, usually brown or purple.

Pancreatic color can be observed subjectively, and the skilled artisan can identify a darkly colored pancreas (which is undesirable, and scores a −1), and a light colored one (which is desirable, and scores a +1); however, a more objective test uses a colorimeter which detects color based upon the ratio of reflected to incident light, the "reflectance ratio." If this is less than about 60, a score of −1 is assigned, whereas one above about 60 is assigned a score of +1.

The third criterion used for the organs was fat content. To determine this, a biopsy sample, about 2×2×0.5 cm thick was immersed in DTZ, for about 5 minutes. Following staining, the tissue was viewed in a dissecting microscope at 10× magnification. Islets appear red, and lipid tissue, green. A field of view was chosen, and the percent of the total area appearing green was estimated. If the total fat content was above about 25%, the organ was assigned a score of −1, whereas a fat content less than about 25% was scored as +1.

It will be understood, of course, that other methodologies are available for determining fat content of an organ, and all can be used herein.

The fourth criterion employed was islet demarcation. For this parameter, the same staining and observation methodology was employed. Those islets that are greater than 50 μm in diameter, were assessed for demarcation. To elaborate, if 2 or more groups of DTZ stained islet cells projected radially from the center of an islet, beyond what is normally a smooth, sharply demarcated external islet border/plane, this resulted in a determination of poor demarcation. If more than 50% of the islets are well demarcated, this criteria was given a score of +1, and if less than 50%, −1.

The final criterion was islet size, which was determined in terms of diameter, relative to the average diameter of islets for the species of animal under consideration. What is determinative for scoring purposes is if the average diameter of the islets in the organ under consideration is greater than average. For many species, the average diameter of islets is approximately 100 microns. This is true for murine, porcine, and human islets, as well as many other species. If the majority of islets examined as described supra were more than 100 μm in diameter, a score of +1 was assigned, whereas a score of −1 was assigned otherwise. If, on the other hand, the average diameter of an islet differs from that of a pig, then the average diameter for that species will be used as the referent. For example, it is well known that tilapia, a variety of fish, have islets that are very large, averaging about 5 mm in diameter. Should a tilapia pancreas be under consideration, then the cutoff point would be 5 mm, and a positive score would be given if the average diameter of the islets was greater than 5 mm.

The scores for these five criteria were tabulated for each pancreas that was examined. If the total score was +1 or higher, the organ was deemed a suitable islet donor.

Exemplary results for ten organs which had total scores of +1 or higher are presented in the table which follows.

TABLE 1

Biopsy Score of Individual Donor Pancreases

| Lot # | WIT | Color | Fat | Islet Size | Demarcation | Biopsy Score |
|---|---|---|---|---|---|---|
| W1561 | 1 | 1 | 1 | 1 | −1 | 3 |
| O2109 | 1 | 1 | 1 | 1 | 1 | 5 |
| Y8641 | 1 | 1 | 1 | 1 | −1 | 3 |
| O37360 | 1 | 1 | 1 | 1 | −1 | 3 |
| O786 | 1 | 1 | 1 | 1 | −1 | 3 |
| Y8587 | 1 | 1 | 1 | −1 | −1 | 1 |
| W1102 | 1 | 1 | 1 | −1 | −1 | 1 |
| W1524 | 1 | 1 | 1 | −1 | 1 | 3 |
| O39820 | 1 | 1 | −1 | −1 | 1 | 1 |
| R2027 | 1 | 1 | 1 | −1 | 1 | 3 |

In the photographs of FIGS. 1A and 1B, micrographs of a pancreas with a score of +3, (FIG. 1A), and a pancreas with a score of −1 (FIG. 1B) are presented, for comparative purposes. In FIG. 1A, large islets (>100 μm) are evident, as is their good demarcation. In contrast, the pancreas depicted in FIG. 1B shows small, poorly demarcated islets.

Under the standards of the protocols described herein, the pancreas depicted in FIG. 1B would not be processed further; however, it was processed for comparative purposes, as is discussed in the examples which follow.

EXAMPLE 2

Following the evaluation set forth in example 1, pancreases with a score of +1 or higher as well as the comparative pancreas with a score of −1, were processed further. The glands were trimmed of fat and connective tissue and then the main pancreatic duct was cannulated with a 16 g, stainless steel, and blunt end needle. A solution of HBSS containing collagenase P, at a concentration of 1.5-2.0 g/l, was perfused at a rate of 50 ml/mm, at 30° C., to provide 2 ml of solution per gram of the pancreas' weight.

The pancreas was then covered with 500 ml HBSS and 2% PS, together with 200 ml of collagenase solution, at 30° C. External circulation of water at 39° C. slowly warmed the organ to 37° C., and kept the digestate temperature at 36-37° C. When the organs appeared dissociated, and offered little resistance to manual pressure (after about 10-20 minutes total time, and 5-10 minutes after reaching 37° C.), digestion was stopped.

Collected digestate was then centrifuged, supernatants aspirated, and the resulting pellet was suspended in 10% PS and an organ preservative solution. Islets were then purified on discontinuous Ficoll, at density gradients of 1.105, 1.095, 1.085 and 1.05 g/cm$^3$, HBSS plus 2% PS, in 50 ml tubes. Tubes were centrifuged at 650 g at 4° C., and islet containing layers were collected, and washed three times, in HBSS plus 10% PS, after which they were manually purified of non-islet tissue with the aid of a dissecting microscope. The islets were resuspended, and two 0.5 ml samples were used for counting islet yield.

For the pancreases shown in FIGS. 1A and 1B, for example, the yield for the pancreas with a +3 value was about 105,000 EIN (Equivalent Islet Number, as defined by Ricordi, et al. supra), at a purity of 98.8%. In contrast, the yield from the organ of FIG. 1B was 44,000 EIN.

The average yield of the ten pancreases of table 1, in fact, was 130,000 EIN, with a mean of 1,101 EIN per gram of digested tissue. Purity, in all cases was over 90%. For 9 of the organs, islet viability was greater than 89%. The methodologies for these determinations are described, infra.

EXAMPLE 3

Following the isolation of the islets, various parameters were determined, including purity and viability, as alluded to supra.

Purity was assessed by staining about 500 EIN with DTZ, for ten minutes, and then standard image analysis was carried out using a dissecting microscope and a digital camera.

Viability was determined by staining a sample with fluorescein diacetate (FDA) and ethidium bromide (EB). To elaborate, about 500 EIN were added to 1 ml of RPM1, 10% PS, and 1% antibiotic/antimyotic ("A/A"). Then, 20 μl of FDA stain that had been made with 10 mg of FDA and 1 ml acetone, and 200 μl of EB that had been made with 30 μl EB and 1 ml PBS were added. Islets were stained, in the dark, for seven minutes, and then random samples of 10-50 islets were viewed with a fluorescent microscope and photographed, to determine viability using standard image analysis.

The insulin content of the islets was also measured, by placing approximately 500 EIN in acid alcohol extraction solution (7.2 ml of 1N HCl, 400 ml of 100% denatured ethanol). Samples were stored at −20° C., and an insulin RIA was carried out.

TABLE 2

| Lot # | Insulin Content (mu/500 EIN) |
|---|---|
| W1561 | 338.66 |
| O2109 | 1288.69 |
| Y8641 | 775.37 |
| O37360 | 402.59 |
| O786 | 184.40 |
| Y8587 | 669.92 |
| W1102 | 590.05 |
| W1524 | ND |
| O39820 | ND |
| R2027 | 474.55 |

EXAMPLE 4

This, and the examples which follow, address the question of whether islets identified as useful and isolated as described, can be used in macrobeads.

Purified islets were resuspended in RPMI 1640+10% PS+1% A/A, to a volume of 2000 EIN/ml. The islets were evenly distributed in tubes, so that each tube contained 1 ml of suspension at 2000 EIN.

Following settling by gravity, supernatants were removed, and 0.5 ml of 1.5% agarose, at 50° C., prepared in minimal essential medium plus 2.5% HEPES buffer, was added to each sample, and mixed evenly. The suspension was then expelled below sterile mineral oil, to make four beads with smooth surfaces and equal islet distributions.

Macrobeads were removed, and washed twice (RPMI+5% PS+1% A/A). These macrobeads were cultured in the same solution, in a humidified 5% $CO_2$ atmosphere, for 5-7 days, after which they were washed, three times, in RPMI+1% A/A, followed by application of a second coat of agarose. For this, 0.5 ml of 5% agarose in MEM, plus HEPES buffer at 60° C., was transferred via pipette, to a sterile plastic spoon, and each macrobead was rolled 3-5 times to produce a uniform, second agarose coating. Following transfer to sterile mineral oil to produce a smooth surface, the macrobeads were removed, washed twice in RPMI+2.5% PS+1% A/A, and incubated at 37° C. in humidified 5% $CO_2$ plus air.

The macrobeads containing encapsulated islets were determined to remain viable for more than 6 months, over which time radioimmunoassays revealed that they continued to produce good levels of insulin.

EXAMPLE 5

This example describes experiments to address the question of whether islets isolated as described will function in vivo.

Male, non-obese diabetic CB17-PrKdc<scid>/J mice, 7-9 weeks old, were used. After a week of acclimation, the animals received 275 mg/kg of streptozotocin, which induces diabetes. Nine days later, when their blood glucose levels averaged over 480 mg/dl, they were started on insulin therapy.

On day 34-35 following administration of streptozotocin, the animals received approximately 1000 EIN of porcine islets, which were transplanted in a blood clot, following Bowen, et al., *Aust. J. Exp. Biol. Med. Sci.,* 58:441-447 (1980), incorporated by reference. In brief, islets were pelleted out of suspension and media were aspirated. Then, about 5-10 µl of blood was taken from the animal, added to the islets, and allowed to clot. The recipient animals were anesthetized with equal volumes of ketamine (167 mg/dl), xylazine (33 mg/ml), and saline. The mixture was administered subcutaneously, at a dose of 0.5 ml/100 g. A small incision was made at the left flank to expose the kidney, and a dissecting microscope was used to make a small incision in the capsule of the kidney. The capsule was then separated from the kidney, the islets/clot were placed under the capsule, the incision was closed, and animals were permitted to recover.

Nephrectomies were performed on the animals, 38-39 days after the transplantation. Briefly, after anesthesia, the graft-bearing kidney was exposed, renal blood vessels were ligated and the kidney of each animal was removed. Five days later, the animals were sacrificed, and pancreases were collected for histological confirmation of complete islet beta cell destruction.

Tissue samples were placed in 10%, neutral buffered formation for 24 hours, and then were transferred to 70% ethyl alcohol.

Following this, the tissues were embedded in paraffin, and 5 µm sections were stained with hematoxylin and eosin. Pancreas and grafted kidney sections were stained for insulin and glucagon containing cells, using standard methods, and were then studied.

All of the mice became normoglycemic after islet grafting. After nephrectomy, the mice all became hyperglycemic, within four days.

The foregoing examples set forth features of the invention, which is a method for evaluating a pancreas to determine if the islets therefrom are therapeutically useful. The method involves assaying at least three of five specified criteria, and assigning a value to each criterion. The value choices, as reported supra are +1 or −1. If, following the three assays, the organ has a score of +3, then the test can be terminated, since even if the final two criteria were to have values of −1, it is not possible for the organ to have a total score of less than +1.

If, after three criteria of the five are determined, and the organ is scored at +1, then a fourth test is carried out, because a score of +1 following three tests does not guarantee a final value of +1 or greater. If the fourth criterion for the organ yields a +1 score, then the test may be considered complete, because, again, it is not possible for the organ to have a score of less than +1 if it has a score of +2 after four tests.

If, after four tests, the organ has a score of 0, then the fifth test should be carried out for a dispositive result.

Conversely, if the organ has a score of −3 after three tests, there is no need to go further, and a score of −2 after four tests eliminates the need for the final test. (Note that, in accordance with the invention, the only possible scores after three tests are +3, +1, −1 or −3, and after four tests, +4, +2, 0 −2 and −4; however, the +4 and −4 scores eliminate the necessity to carry out further tests. Hence, while it may be desirable to do so, it is not required.)

The choice of which three tests to carry out first is up to the skilled artisan; however, the warm ischemia time criterion is one that is within the control of the investigator, and may be preferred as one of the first three tests. The remainder of the first three tests will be the choice of the skilled artisan.

The methodology set forth herein may be used on a pancreas of any species, including but not being limited to, bovine, porcine, ovine, murine, primate, human, piscine or other species.

The islets which are obtained from pancreases that are selected in accordance with the invention may be used, "as is," as is shown by the examples, or may be used, e.g., in encapsulated, macrobead form, as described in U.S. Pat. Nos. 5,643,569 and Re 38,027 both of which are incorporated by reference.

Other aspects of the invention will be clear to the skilled artisan, and need not be elaborated further.

The terms and expression which have been employed are used as terms of description and not of limitation, and there is no intention in the use of such terms and expression of excluding any equivalents of the features shown and described or portions thereof, it being recognized that various modifications are possible within the scope of the invention.

The invention claimed is:

1. A method for determining if a pancreas isolated from a member of a species will be a source of therapeutically useful islets, comprising:
    (i) determining warm ischemia time of said isolated pancreas, and at least two of:
    (ii) determining color of said isolated pancreas,
    (iii) determining fat content of said isolated pancreas,
    (iv) determining demarcation of islets in said pancreas, and
    (v) determining average size of islets isolated from said isolated pancreas, wherein:
    (a) in (i) a warm ischemia time of 20 minutes or less is assigned a score of +1, and one greater than 20 minutes is assigned a score of −1;
    (b) in (ii), determining color comprises determining a reflectance ratio and if said reflectance ratio is 60 or more, assigning a score of +1, and if said ratio is less than 60 assigning a score of −1;
    (c) a fat content below 25% is assigned a score of +1, and 25% or above is scored at −1;
    (d) in (iv), determining demarcation comprises assessing demarcation of islets and assigning a score of +1, if more than 50% of islets are well demarcated and assigning a score of −1 if 50% or less of islets are well demarcated, and
    (e) an average diameter for islets equal to or greater than the average value for said species is assigned a score of +1, and an average diameter for islets below the average value for said species is assigned a score of −1, and
    (f) comprising adding the scores obtained in (a) through (e), whereby a final positive score indicates said pancreas is a source of therapeutically useful islets.

2. The method of claim 1, comprising (i) and at least three of (ii)-(v).

3. The method of claim 1, comprising all of (i) to (v).

4. The method of claim 1, comprising (i), (ii) and (iii).

5. The method of claim 1, comprising (i), (ii) and (iv).

6. The method of claim 1, comprising (i), (ii) and (v).

7. The method of claim 1, comprising (i), (iii) and (iv).

8. The method of claim 1, comprising (i), (iii) and (v).

9. The method of claim 1, comprising (i), (iv) and (v).

10. The method of claim 2, comprising (i)-(iv).

11. The method of claim 2, comprising (i), (ii), (iii) and (v).

12. The method of claim 2, comprising (i), (ii), (iv) and (v).

13. The method of claim 2, comprising (i) and (iii)-(v).

* * * * *